United States Patent
Wei

[11] Patent Number: 6,123,946
[45] Date of Patent: Sep. 26, 2000

[54] HYGIENIC BAG AND PREPARATION THEREOF

[76] Inventor: Lingyi Wei, No. 99 Xijie Street, Emeishan City, Sichuan Province, 614200, China

[21] Appl. No.: 09/142,651
[22] PCT Filed: Mar. 11, 1997
[86] PCT No.: PCT/CN97/00017
  § 371 Date: Apr. 12, 1999
  § 102(e) Date: Apr. 12, 1999
[87] PCT Pub. No.: WO97/33549
  PCT Pub. Date: Sep. 18, 1997

[30] Foreign Application Priority Data

Mar. 12, 1996 [CN] China ................................. 96117477

[51] Int. Cl.⁷ ........................... A01N 65/00; A61K 9/14
[52] U.S. Cl. ..................................... 424/195.1; 424/489
[58] Field of Search ............................. 424/195.1, 400, 424/402, 489

[56] References Cited

FOREIGN PATENT DOCUMENTS

| | | |
|---|---|---|
| 2150857 | 12/1993 | China . |
| 1080857 | 1/1994 | China . |
| 1083374 | 3/1994 | China . |
| 1100960 | 4/1995 | China . |

OTHER PUBLICATIONS

Duke, James A. and Ayensu, Edward S., Medicinal Plants of China, vol. 1, p. 77, and 124, 1985.

*Primary Examiner*—Thurman K. Page
*Assistant Examiner*—Susan Tran
*Attorney, Agent, or Firm*—Tilton, Fallon, Lungmus & Chestnut

[57] ABSTRACT

The present invention relates to a health-protective bag which contains: 30–50% by weight of rice, of which at least 30% has been soaked in an aqueous extract of a Chinese herb composition; 20–30% by weight of grain(s) selected from the group consisting of sorghum, beans, panicum miliaceum and millet, of which at least 30% by weight has been soaked in an aqueous extract of another Chinese herb composition; and 20–50% by weight of a pulverous Chinese herb composition. The present invention also provides a process for producing the said health-protective bag.

10 Claims, No Drawings

6,123,946

HYGIENIC BAG AND PREPARATION THEREOF

CLAIM TO PRIORITY

This invention is entitled to priority based on China Patent Application No. 96117477.3, filed Mar. 12, 1996, through International Application No. PCT/CN97/00017, filed Mar. 11, 1997.

FIELD OF THE INVENTION

The present invention relates to a health-protective bag and a process for producing the same, particularly relates to a health-protective bag containing grains and a Chinese herb composition and a process for producing the same.

BACKGROUND OF THE INVENTION

With the rhythm of modern life becoming faster and faster, people long for a simple method to strengthen their health with an inexpensive but effective articles. With the raising of living standards, people more and more wish for long life, beatify and the strengthening of their immunity against diseases etc. Chinese medicine has a long history. Recently, many scholars who did a vast amount of research on Chinese herbs, developed many articles for health protection. Professor Laihue WU, from The Institute For Inflections and Infirmities of Old Age in Xianyang, Shanxi province, designed a health-protective bag under the name "505 Shen Gong Yuan Qi Dai", which is quite popular nowadays. This article can be disposed at different parts of a human body, such as the breast, the back, the abdomen, etc. of a human body. The active substance of the herbs contained in the bag, by permeating through the bag, effects the strengthening of the body and immunity.

Chinese patent application CN 1054895 A discloses "A process for producing a Shen Gong Yuan Qi Dai", which comprises soaking a powder mixture consisting of 15 expensive ingredients of ginseng, American Ginseng, the body of *Cordyceps sinensis* Sacc. etc. with Sorghum liquor in a porcelain jar underground; soaking a mixture of 45 Chinese herbs of bees venom, A. sieboldii Mig etc. with the liquid as obtained, steaming, drying in coolness and pulverizing to powder; and finally wrapping the obtained powder in a cotton cloth. The such produced "Yuan Qi Dai" is tied to cover the acupuncture point "shen jue" located right at the navel.

Chinese patent application CN 1091042 A discloses a "Chinese herb health-protective bag, a process for producing the same and its use". Said health-protective bag contains the following Chinese herbs; Ginseng, *Loranthus parasiticus* (L.) Merr., *Atractylodes macrocephala koidz, Artemisia argyi* Levl. et vant, Astragalusmembranaceus (Fisch.) Bunge, *Amomum villosum* Lour, *Scutellaria baicalensis* Georgi, *Agastache rugosa* (Fisch. et May.) Oktze, *Eucommia ul moides, Codonopsis pilosula* (Franch.) Nannf, *Angelica sinensis* (Oliv) Diels, *Paeonia lactiflora* Pall, *R. glutinosa* Libosch, *Dioscorea opposita* Thunb, *Lycium barbarum* L., *Ligustrum lucidum* Ait, *Cinnamomum cassis* Presl., *Poria cocos* (Schw) wolf., *Zizyhus jujuba* Mill. var. Spinosa Hu., *Glycyrrhiza uralensis* Fisch, etc. It is mainly used for preventing and opposing weakness during pregnancy, problems in early pregnancy; fetus abnormal development, abnormal presentations, threatened abortion, abortion, habitual abortion and other problems during pregnancy.

As mentioned above, the health-protective products in the prior art are only effective on parts of the body where they are attached. For other parts of the body, especially head and limbs, their abilities fall short of their wishes.

Furthermore, these kinds of health-protective products rely on the permeation of the active substances of the herb components, the people who have the wish to do something for their health, remain passive.

OBJECTS OF THE INVENTION

The object of the present invention is to overcome the shortcomings of health-protective products in the prior art by providing a health-protective bag which can act on any parts of the human body.

Another object of the present invention is to provide a process for producing the health-protective bag of the present invention.

SUMMARY OF THE INVENTION

According to the first aspect of the present invention, it provides a health-protective bag which comprises a cotton bag and a composition contained in the bag, said composition comprises the following components:

(1). 30–50% by weight of rice, wherein the least 30% of the rice has been soaked with an aqueous extract of the following Chinese herb composition for about 1 to 3 hours:
13.00–14.00% *Mellia toosendan* Sieb. et Zucc. 13.00–14.00% *Chrysanthemum morifolium* Ramat, (also known as *Chrysanthemum indicum*) 7.60–8.60% *Lespedeza cuneata* (Dum. Cours.), 3.50–4.50% *Phyllostachys nigra* var. henonis (Miff.) Stapf. ex Rendle, 13.00–14.00% *Milletia reticulata* Benth, 13.00–14.00% *Lygodium japonicum.* (Thunb.) Sw., 7.60–8.60% Shi Xian Tao (also known as *Pholidota chinesis*), 13.00–14.00% *Rheum palmatum* L., 7.60–8.60% *Cibotium barometz* (L.) J. Sm., 3.50–4.50% *Zingiber officinale* Rose, wherein all the percentages are weight percentages, and then dried after filtration;

(2). 20–30% by weight of at least one grain selecting from the group consisting of Sorghum, Beans, panicum miliaceum and millet, wherein, at least 30% by weight of the grain has been soaked with an aqueous extract of the following Chinese herb composition for about 24–72 hours:
40.60–41.60% Bai Cao Shuang, 8.00–8.40% Bamboo blossoms, 13.20–14.20% *Polygonum multiflorum* Thumb, 4.00–4.20% SnS (also known at Realgar), 4.00–4.20% *Manis pentadactyla* L., 8.00–8.40% Tea leaves and 20.00–21.00% *Ziziphus jujuba* Mill, wherein all the percentages are weight percentages, and then dried after filtration;

(3). 20–50% by weight of a pulverous Chinese herb composition containing the following components:
1.5–2.5% *Panax psuedo ginseng* Wall. var notoginseng (Burk.) Hoo et Tseng, 6.5–7.5% *Rheum palmatum* L., 3.0–4.0% *Aquilaria agallochah* Roxdb, 3.0–4.0% *Angelica sinensis* (Oliv) Diels, 3.0–4.0% Saussurea Lappa Clarke, 4.8–5.5% *Manis pentadactyla* L., 2.7–3.5% Carthamus Tinctoprius L., 2.7–3.5% *Prunus persica*, 4.8–5.5% *Procirus trifoliata* (L.) Raf. 4.8–5.5% *Notopterygium incisium* Ting, 4.8–5.5% *Eucommia ulmoides,* 4.8–5.5% Cinnamomum Cassia presl., 3.0–4.0% *Achyrantes bidentata* Bl., 1.5–2.5% *Kochia scoparia* (L.) Schrad., 3.0–4.0% *Saposhnikovia divaricata*

(Turcz.) Schisch K., 4.8–5.5% *Melia toosendan* sidb. et Zucc, 3.0–4.0% *Schizandra chinensis* Baill., 10.0–11.1% *Lycopodium clavatum* L., 2.7–3.5% *Vaccaria pyramidata* Medic (also known as *Vaccaria segetalis*), 4.8–5.5% *Lespedeza cuneata* (Dum. Cours.), 1.0–1.5% *Blumea balsamifera* DC., 4.8–5.5% *Periploca sepium* Bge., 3.0–4.0% *Phyllostachis nigra* var. henonis (Miff.) Stapf. ex Rendle, wherein all the percentages are on the basis of the total weight of said composition.

According to the present invention, the rice is preferably the one which has been stored for at least three years.

According to the second aspect of the present invention, it provides a process for producing the health-protective bag of the present invention, which comprises the following steps:

(1) selecting a rice free from mildew and mould, wherein at least 30% by weight of which is treated according to the following method:
  (a) cooking the following Chinese herb composition in water for 1 to 3 hours:
    13.00–14.00% *Melia toosendan* Sieb. et Zucc, 13.00–14.00% *Chyrsanthemum mouifolium* Ramat, 7.60–8.60% *Lespedeza cuneata* (Dum. Cours.), 3.50–4.50% *Phyllostachys nigra* var. henonis (Miff.) Stapf. ex Rendle, 13.00–14.00% *Milletia reticulata* Benth, 13.00–14.00% *Lygodium japonicum.* (Thunb.) Sw., 7.60–8.60% Shi Xian Tao, 13.00–14.00% *Rheum palmatum* L., 7.60–8.60% *Cibotium barometz* (L.) J. Sm., 3.50–4.50% *Zingiber officinale* Rose, wherein all the percentages are weight percentages; filtering the mixture after cooing to remove solid materials to obtain an aqueous extract of said composition;
  (b) soaking the rice with the aqueous extract obtained in the above step (a) at a weight ratio of aqueous extract:rice=30–50:70–50 for about 1–3 hours, drying the soaked rice after filtration;

(2) selecting at least one grain from the group consisting of whether sorghum, beans, panicum miliaceum and millet, wherein at least 30% by weight of which is treated according to the following method:
  (a) cooking the following Chinese herb composition in water for about 1 to 3 hours:
    40.60–41.60% Bai Cao Shuang, 8.00–8.40% Bamboo blossoms, 13.20–14.20% *Polygonum multiflorum* Thumb, 4.00–4.20% SnS, 4.00–4.20% *Manis pentadactyla* L., 8.00–8.40% Tea leaves and 20.00–21.00% *Ziziphus jujuba* Mill, wherein all the percentages are weight percentages; filtering the mixture after cooling to remove solid materials to obtain an aqueous extract of said composition;
  (b) soaking the selected grain(s) with the aqueous extract obtained in the above step (a) at a weight ratio of aqueous extract:grain(s)=40–60:60–40 for about 24–72 hours, drying the soaked grain(s) after filtration;

(3) pulverizing the following components respectively: *Panax pseudo ginseng* Wall. var. notoginseng (Burk.) Hoo et Tseng, *Rheum palmatum* L., *Aquilaria agallochah* Roxdb, *Angelica sinensis* (Oliv) Diels, *Saussurea Lappa* Clarke, *Manis pentadactyla* L., *Prunus persica, Pocirus trifoliata* (L.) Raf., *Notopterygium incisium* Ting, *Eucommia ulmoides,* Cinnamomum Cassia presl., *Achyrantes bidentata* Bl., *Kochia scoparia* (L.) Schrad, *Saposhnikovia divaricata* (Turcz.) Schisch K., *Melia toosendan* Sieb. et Zucc, *Schizandra chinensis* Baill., *Lycopodium clavatum* L., *Vaccaria pyramidata* Medic, *Lespedeza cuneata* (Dum. Cours.), *Blumea balsamifera* DC., *Periploca sepium* Bge, *Phyllostachis nigra* var. henonis (Miff.) Stapf. ex Rendle to powders having particle size in the range of about 0.06 mm–0.10 mm, mixing these powders according to the following proportion to obtain a powder mixture.

1.5–2.5% *Panax pseudo ginseng* wall. var notoginseng (Burk.) Hoo et Tseng., 6.5–7.5% *Rheum palmatum* L., 3.0–4.0% *Aquilaria agallochah* Roxdb, 3.0–4.0% *Angelica sinensis* (Oliv) Diels, 3.0–4.0% *Saussurea Lappa* Clarke, 4.8–5.5% *Manis pentadactyla* L., 2.7–3.5% *Carthamus tinctorius* L., 2.7–3.5% *Prunus persica,* 4.8–5.5% *Procirus trifoliata* (L.) Raf., 4.8–5.5% *Notopterygium incisium* Ting, 4.8–5.5% *Eucommia ulmoides,* 4.8–5.5% Cinnamomum Cassia presl., 3.0–4.0% *Achyrantes bidentata* Bl., 1.5–2.5% *Kochia scoparia* (L.) Schrad., 3.0–4.0% *Saposhnikovia divaricata* (Turcz.) Schisch K., 4.8–5.5% *Melia toosendan* Sieb. et Zucc, 3.0–4.0% *Schizandrs chinensis* Baill., 10.1–11.1% *Lycopodium clavatum* L., 2.7–3.5% *Vaccaria pyramidata* Medic, 4.8–5.5% *Lespedeza cuneata* (Dum. Cours.), 1.0–1.5% *Blumea balsamifera* DC., 4.8–5.5% *Periploca sepium* Bge., 3.0–4.0% *Phyllostachis nigra* var. henonis (Miff.) Stapf. ex Rendle, wherein all the percentages are weight percentages;

(4) mixing thoroughly the rice, the grain(s) and the pulverous Chinese herbs composition obtained in the above steps (1), (2) and (3) respectively according to a weight ratio of 30–50:20–30:20–50;

(5) filling the composition obtained in step (4) into a pure cotton bag.

According to the process of the present invention, the rice is preferably the one which has been stored for at least three years.

DETAILED DESCRIPTION OF THE INVENTION

The present invention relates to a health-protective bag, which comprises a pure cotton bag and a composition contained therein, and the said composition contains the following components:

(1). 30–50% by weight of rice, wherein at least 30% of the rice has been soaked with an aqueous extract of the following Chinese herb composition for about 1–3 hours:
  13.00–14.00% *Mellia toosendan* Sieb. et Zucc, 13.00–14.00% *Chrysanthemum morifolium* Ramat, 7.60–8.60% *Lespedeza cuneata* (Dum. Cours.), 3.50–4.50% *Phyllostachys nigra* var. henonis (Miff.) Stapf. ex Rendle, 13.00–14.00% *Milletia reticulata* Benth, 13.00–14.00% *Lygodium japonicum* (Thumb.) Sw., 7.60–8.60% Shi Xian Tao, 13.00–14.00% *Rheum palmatum* L., 7.60–8.60% *Cibotium barometz* (L.) J. Sm., 3.50–4.50% *Zingiber officinale* Rose, wherein all the percentages are weight percentages, and then dried after filtration;

(2) 20–30% by weight of at least one grain selected from the group consisting of Sorghum, Beans, panicum miliaceum and millet, wherein, at least 30% by weight of the grain has been soaked with an aqueous extract of the following Chinese herb composition for about 24–72 hours:
  40.60–41.60% Bai Cao Shuang, 8.00–8.40% Bamboo blossoms, 13.20–14.20% *Polygonum multiflorum* Thumb, 4.00–4.20% SnS, 4.00–4.20% *Manis pen-*

*tadactyla* L., 8.00–8.40% Tea leaves and 20.00–21.00% *Zizyphus jujuba* Mill, wherein all the percentages are weight percentages, and then dried after filtration;

(3). 20–50% by weight of pulverous Chinese herb composition containing the following components:

1.5–2.5% *Panax pseudo ginseng* Wall. var notoginseng (Burk.) Hoo et Tseng, 6.5–7.5% *Rheum palmatum* L., 3.0–4.0% *Aquilaria agallochah* Roxdb, 3.0–4.0% *Angelica sinensis* (Oliv) Diels, 3.0–4.0% Saussurea Lappa Clarke, 4.8–5.5% *Manis pentadactyla* L., 2.7–3.5% Carthamus Tinctoprius L., 2.7–3.5% *Prunus persica,* 4.8–5.5% *Procirus trifoliata* (L.) Raf., 4.8–5.5% *Notopterygium incisium* Ting, 4.8–5.5% *Eucommia ulmoides,* 4.8–5.5% Cinnamomum Cassia presl., 3.0–4.0% *Achyrantes bidentata* Bl., 1.5–2.5% *Kochia scoparia* (L.) Schrad., 3.0–4.0% *Saposhnikovia divaricata* (Turcz.) Schisch K., 4.8–5.5% *Milia toosendan* sidb. et Zucc. 3.0–4.0% *Schizandra chinensis* Baill., 10.1–11.1% *Lycopodium clavatum* L., 2.7–3.5% *Vaccaria pyramidata* Medic, 4.8–5.5% *Lespedeza cuneata* (Dum. Cours.), 1.0–1.5% *Blumea balsamifera* DC., 4.8–5.5% *Periploca sepium* Bge., 3.0–4.0% *Phyllostachis nigra* var. henonis (Miff.) Stapf. ex Rendle, wherein all the percentages are on the basis of the total weight of said composition.

According to the present invention, the rice is preferably the one which has been stored for at least three years.

According to the present invention, the health-protective bag preferably contains 35–45% by weight of rice, 15–25% by weight of at least one grain selected from the group consisting of whether sorghum, beans, panicum miliacum and millet, and 30–40% by weight of a pulverous Chinese herb composition.

Research done in physics of modern medicine revealed that the innate character of sickness of connected to a blockade of Qi (energy) on the meridians. When Qi and blood cannot easily circulate, the pathological products silt up, the inner organs suffer from a lack of nutrition, thus disorder the metabolism and cause diseases. Another view holds that the disorder of the human life-information is the reason why sickness is attached. According to this view, the bad information from the inner environment of the human body (psychological and physical) as well as from the outer environment of the human body (biological: microorganisms, plants, animals and the human body, physical and chemical) disturb or even destroy the normally healthy information of the human body. Therefore, it is called the disorder of the human life information. Only by adjusting the disordered information of the human, can many diseases be radically cured.

The present invention has been accomplished on the basis of modern medicine pathology theory. People can use the health-protective bag of the present invention to pat and massage their meridians and points gradually from the surface to inner, from shallow into deeper. By taking advantage of the absorption ability of sin and acupuncture points, the active substance (Qi) of the grains and herbs contained in the health-protective bag of the present invention permeate from the surface of the skin to the inner body, and adjust the function of the inner organs.

One main component of the health-protective bag of the present invention is rice. The character of rice is sweet and mild, governing the stomach and the spleen (symbol for the system of digestion in Traditional Chinese Medicine,). Rice nurtures our roots of vital energy. It strengthens our spleen and benefits our energy (Qi), nourishes and keeps our naturally good looks and beauty. The rice used in the present invention is preferably the one which has been stored for at least three years.

According to the present invention, the Chinese herb composition powder contained in the bag preferably comprises:

1.8–2.2% *Panax pseudo ginseng* Wall. var. notoginseng (Burk.) Hoo et Tseng, 6.8–7.2% *Rheum palmatum* L., 3.3–3.7% *Aquilaria agallochah* Roxdb, 3.3–3.7% *Angelica sinensis* (Oliv) Diels, 3.3–3.7% Saussurea Lappa Clarke, 5.1–5.3% *Manis pentadactyla* L., 3.0–3.2% *Carthamus tinctorius* L., 3.0–3.2% *Prunus persica,* 5.1–5.2% *Procirus trifoliata* (L,) Raf., 5.1–5.3% *Notopterygium incisium* Ting, 5.1–5.3% *Eucommia ulmoides,* 5.1–5.3% Cinnamomum Cassia presl., 3.3–3.7% *Achyrantes bidentata* Bl., 1.8–2.2% *Kochia scoparia* (L.) Schrad., 3.3–3.7% *Saposhnikovia divaricata* (Turcz.) Schisch K., 5.1–5.3% *Melia toosendan* Sieb. et Zucc, 3.3–3.7% *Schizandra chinensis* Baill., 10.4–10.8% *Lycopodium clavatum* L., 3.0–3.3% *Vaccaria pyrmidata* Medic, 5.1–5.3% *Lespedeza cuneata* (Dum. Cours.), 1.2–1.4% *Blumea balsamifera* DC., 5.1–5.3% *Periploca sepium* Bge., 3.3–3.7% *Phyllostachis nigra* var. henonis (Miff.) Stapf. ex Rendle, wherein all the percentages are weight percentages.

According to the health-protective bag of the present invention, the components and proportions as contained in the Chinese herb composition powder can be adjusted according to personal health condition, e.g., for weaker and older persons, *Astragalus membranaceus* (Fisch.) Bunge and ginseng can be further added. The method of adjusting the components and the proportions in the Chinese herb composition is obvious to those skilled in the art.

According to the health-protective bag of the present invention, the color of the cotton bag can be white, black, green, yellow or red. People who use the health-protective bag of the present invention can personally choose the color which will shit their personal health condition. If, for example, people have problems with the heart, they are advised to choose the health-protective bag of the present invention in red color. If their livers (in Traditional Chinese Medicine the seat for the element fire) have too much heat, ensuing hypertension, hyperlipoidemia, arteriosclerosis, they will be advised to choose the health-protective bag of the present invention in black or green color. If people suffer from digestion problems such as gastroenteritis, they can choose the health-protective bag of the present invention in yellow color. If energy (Qi) from their livers is blocked, and damp heat is silted up ensuing hepatic calculus, hepatocirrhosis, then they are advised to choose the health-protective bag of the present invention in green or yellow color.

According to the second aspect of the present invention, it provides a process for producing the said health-protective bag of the present invention, which comprises the following steps:

(1) selecting a rice free form mildew and mould, wherein at least 30% by weight of which is treated according to the following method:

(a) cooking the following Chinese herb composition in water for 1 to 3 hours:

13.00–14.00% *Melia toosendan* Sieb. et Zucc, 13.00–14.00% *Chrysanthemum mouifolium* Ramat, 7.60–8.60% *Lespedeza cuneata* (Dum. Cours.), 3.50–4.50% *Phyllostachys nigra* var. henonis (Miff.) Stapf. ex Rendle, 13.00–14.00%

*Milletia reticulata* Benth, 13.00–14.00% *Lygodium japonicum.* (Thunb.) Sw., 7.60–8.60% Shi Xian Tao, 13.00–14.00% *Rheum palmatum* L., 7.60–8.60% *Cibotium barometz* (L.) J. Sm., 3.50–4.50% *Zingiber officinale* Rose, wherein all the percentages are weight percentages; filtering the mixture after cooling to remove solid materials to obtain an aqueous extract of said composition;

(b) soaking the rice with the aqueous extract obtained in the above step (a) at a weight ratio of aqueous extract:rice=30–50:70–50 for about 1–3 hours, drying the soaked rice after filtration;

(2) selecting at least one grain from the group consisting of whether sorghum, beans, panicum miliceum and millet, wherein at least 30% by weight of which is treated according to the following method:

(a) cooking the following Chinese herb composition in water for about 1 to 3 hours;

40.60–41.60% Bai Cao Shuang, 8.00–8.40% Bamboo blossoms, 13.20–14.20% *Polygonum multiflorum* Thumb, 4.00–4.20% SnS, 4.00–4.20% *Manis pentadactyla* L., 8.00–8.40% Tea leaves and 20.00–21.00% *Zizyphus jujuba* Mill, wherein all the percentages are weight percentages; filtering the mixture after cooling to remove solid materials to obtain an aqueous extract of said composition;

(b) soaking the selected grain(s) with the aqueous extract obtained in the above step (a) at a weight ration of aqueous extract:grain(s)=40–60:60–40 for about 24–72 hours, drying the soaked grain(s) after filtration;

(3) pulverizing the following components respectively: *Panax pseudo ginseng* Wall. var. notoginseng (Burk.) Hoo et Tseng., *Rheum palmatum* L., *Aquilaria agallochah* Roxdb, *Angelica senensis* (Oliv) Diels, Saussurea Lappa Clarke, *Manis pentadactyla* L., Carthamus Tinctorius L., *Prunus persica, Pocirus trifoliata* (L.) Raf., *Notopterygium incisium* Ting, *Eucommia ulmoides,* Cinnamomum Cassia presl., *Achyrantes bidentata* Bl., *Kochia scoparia* (L.) Schrad., *Saposhnikovia divaricata* (Turcz.) Schisch K., *Melia toosendan* Sieb, et Zucc, *Schizandra chinensis* Baill., *Lycopodium clavatum* L., *Baccaria pyramidata* Medic, *Lespedeza cuneata* (Dum. Cours.), *Blumea balsamifera* DC., *Periploca sepium* Bge., *Phyllostachis nigra* var. henonis (Miff.) Stapf. ex Rendle to make powders having particle size in the range of about 0.06 mm–0.10 mm, mixing these powders according to the following proportion to obtain a powder mixture:

1.5–2.5% *Panax pseudo ginseng* Wall. var notoginseng (Burk.) Hoo et Tseng, 6.5–7.5% *Rheum palmatum* L., 3.0–4.0% *Aquilaria agallochah* Roxdb, 3.0–4.0% *Angelica sinensis* (Oliv) Diels, 3.0–4.0% Saussurea Lappa Clarke, 4.8– 5.5% *Manis pentadactyla* L., 2.7–3.5% *Carthamus tinctorius* L., 2.7–3.5% *Prunus persica,* 4.8–5.5% *Procirus trifoliata* (L.) Raf., 4.8–5.5% *Notopterygium incisium* Ting, 4.8–5.5% *Eucommia ulmoides,* 4.8–5.5% Cinnamomum Cassia presl., 3.0–4.0% *Achyrantes bidentata* Bl., 1.5–2.5% *Kochia scoparia* (L.) Schrad, 3.0–4.0% *Saposhnikovia divaricata* (Turcz.) Schisch K., 4.8–5.5% *Melia toosendan* Sieb. et Zucc, 3.0–4.0% *Schizandra chinensis* Baill., 10.0–11.1% *Lycopodium clavatum* L., 2.7–3.5% *Vaccaria pyramidata* Medic, 4.8–5.5% *Lespedeza cuneata* (Dum. Cours.), 1.0–1.5% *Blumea balsamifera* DC., 4.8–5.5% *Periploca sepium* Bge., 3.0–4.0% *Phyllostachis nigra* var. henonis (Miff.) Stapf. ex Rendle, wherein all the percentages are weight percentages;

(4) mixing thoroughly the rice, the grain(s) and the Chinese herbs powder composition obtained in the above steps (1), (2) and (3) respectively according to a weight ratio of 30–50:20–30:20–50;

(5) filling the composition obtained in step (4) into a pure cotton bag.

According to the process of the present invention, the rice as used is preferably the one which has been stored for at least three years.

According to the process of the present invention, the Chinese herb composition powder contained in the bag preferably comprises:

1.8–2.2% *Panax pseudo ginseng* Wall. var. notoginseng (Burk.) Hoo et Tseng, 6.8–7.2% *Rheum palmatum* L., 3.3–3.7% *Aquilaria agallochah* Roxdb, 3.3–3.7% *Angelica sinensis* (Oliv) Diels, 3.3–3.7% Saussurea Lappa Clarke, 5.1–5.3% *Manis pentadactyla* L., 3.0–3.2% *Carthamus tinctorius* L., 3.0–3.2% *Prunus persica,* 5.1–5.2% *Procirus trifoliata* (L.) Raf., 5.1–5.3% *Notopterygium incisium* Ting, 5.1–5.3% *Eucommia ulmoides,* 5.1–5.3% Cinnamomum Cassia presl., 3.3–3.7% *Achyrantes bidentata* Bl., 1.8–2.2% *Kochia scoparia* (L.) Schrad., 3.3–3.7% *Saposhnikovia divaricata* (Turcz.) Schisch K., 5.1–5.3% *Melia toosendan* Sieb. et Zucc, 3.3–3.7% *Schizandra chinensis* Baill., 10.4–10.8% *Lycopodium clavatum* L., 3.0–3.3% *Vaccaria pyramidata* Medic, 5.1–5.3% *Lespedeza cuneata* (Dum. Cours.), 1.2–1.4% *Blumea balsamifera* DC., 5.1–5.3% *Periploca sepium* Bge., 3.3–3.7% *Phyllostachis nigra* var. henonis (Miff.) Stapf. ex Rendle, wherein all the percentages are weight percentages.

Instruction of how to use the health-protective bag of the present invention are as follows.

Generally speaking, the method of using the health-protective bag is to pat the related parts of the body with the bag. For example, patting the head can soften the blood vessels and improve blood circulation of the head. It is quite helpful for curing and rehabilitating cerebrovascular and diseases of the nervous system, such as for cerebral thrombosism encephalorrhahia, paraloysis, facial paralysis, etc. Patting the acupuncture point Bai Hui (Located on the meridian Du Mai in the middle of the head) can cure headache, dizziness, apuhasia, epilepsy, mental problems, insomnia, prolapse of rectum, etc. If one preservers for a long term in patting the Bai Hui point using the health-protective bag of the present invention, one can develop the potentials of the brain, fortify the agility of mind, enhance the memory, harmonize the function of the left and right spheres of the brain. Patting on the back causes the Jing Qi (essence of the body) to brim and be vigorous, thereby normalizing the kidneys, the urine bladder, intestines, colon, gynecopathy and other genital problems. It can cure costalgia, jaundice vomitting, diarrhea, oedema, etc. It is also very helpful for curing liver, gallbladder, spleen and stomach diseases. Patting in the area of the scapulae and the Dazhui (located below the 7th vertebrae) can cure cough, asthma, angia pectoris and heart stroke, palpitation, insomnia, etc. Patting the lower belly is very effective for curing weakness, splanchnoptosis caused by kidney, genital and urinary. It is very effective for curing gynecopathy. Patting the costae can remove stagnancy of the vital energy of the liver and restore the normal function of a depressed liver, strengthen the spleen's function. Patting the stomach can regulate the Liu Fu (in Traditional Chinese Medicine, it means the intestines colon, gallbladder, urinary bladder, stomach and san jiao, system of digestion). Patting the thighs relatively quick activates the Qi on the meridians and has an obvious erect on atrophia and paralysis. Patting the Wei Zong point (located on the urinary bladder meridian, behind the knee), not only has an obvious effect on ishias lumbago, but is also good for the kidneys, the urinary bladder and other urinary system problems. Patting the point Huan Tiao (located on the hip, where the bladder meridian and gall bladder meridian cross) and the point Cheng Shan can heal ishias, arthritis, chronic strain. Patting the point Yang Ling Quan (located on the gall meridian, below the knee) has an effect on curing acute and chronicle pains of the costae and lower belly.

BEST MODES FOR CARRYING OUT THE INVENTION

The present invention will be further explained in reference with the Examples given below.

Example 1

(1) The following Chinese herbs were pulverized respectively:

Panax pseudo ginseng Wall. var. notoginseng (Burk.) Hoo et Tseng, Rheum palmatum L. Aquilaria agallochah Roxdb, Angelica sinensis (Oliv) Diels, Saussurea Lappa Clarke, Manis pentadactyla L., Carthamus Tinctoprius L., Prunus persica, Pocirus trifoliata (L.) Raf., Notopterygium incisium Ting, Eucommia ul moides, Cinnamomum Cassia presl., Achyrantes bidentata Bl., Kochia scoparia (L.) Schrad., Saposhnikovia divaricata (Turcz.) Schisch K., Melia toosendan Sieb. et Zucc, Schizandra chinensis Baill., Lycopodium clavatum L., Vaccaria pyramidata Medic, Lespedeza cuneata (Dum. Cours.), Blumea balsamifera DC., Periploca sepium Bge., Phyllostachis nigra var. henonis (Miff.) Stapf. ex Rendle to obtain their powders having a size in the range of 0.06 mm–0.10 mm respectively. These powders were mixed homogeneously according to the following proportion: 6 g Panax pseudo ginseng Wall. Var. notoginseng (Burk.) Hoo et Tseng, 20 g Rheum palmatum L., 10 g Aquilaria agallochah Roxdb, 10 g Angelica sinensis (Oliv) Diels, 10 g Saussurea Lappa Clarke, 15 g Manis pentadactyla L., 9 Carthamus tinctorius L., 9 g Prunus persica, 15 g Procirus trifoliata (L.) Raf., 15 g Notopterygium incisium Ting, 15 g Eucommia ulmoides, 15 g Cinnamomum Cassia presl., 10 g Achyrantes bidentata Bl., 6 g Kochia scoparia (L.) Schrad., 10 g Saposhnikovia divaricata (Turcz.) Schisch K., 15 g Melia toosendan Sieb. Et Zucc, 10 g Schizandra chinensis Baill., 30 g Lycopodium clavatum L., 9 g Vaccaria pyramidata Medic, 15 g Lespedeza cuneata (Dum. Cours.), 3 g Blumea balsamifera DC., 15 g Periploca sepium Bge., 10 g Phyllostachis nigra var. henonis (Miff.) Stapf. ex Rendle to obtain a powder Chinese herb composition.

(2) A Chinese herb composition comprising the following components was cooked in 800 ml water for two hours:

10 g Melia toosendan Sieb. et Zucc, 10 g Chrysanthemum morifolium Ramat, 6 g Lespedeza cuneata (Dum. Cours.), 3 g Phyllostachys nigra var. henonis (Miff.) Stapf. ex Rendle, 10 g Milletia reticulata Benth, 10 g Lygodium japonicum. (Thumb.) Sw., 6 g Shi Xian Tao, 10 g Rheum palmatum L., 6 g Cibotium barometz (L.) J. Sm., and 3 g Zingiber officinale Rose. The obtained mixture was cooled and filtered to remove solid materials to obtain about 160 ml aqueous extract of the composition. 500 g pure rice, free form mildew and mould was used. 200 g of the rice was soaked in the aqueous extract obtained above for two hours. Then, the mixture was filtered and dried.

(3) A Chinese herb composition comprising the following components was cooked in 700 ml water for two hours:

30 g Bai Cao Shuang, 6 g Bamboo blossoms, 10 g Ploygonum multiflorum Thumb, 3 g SnS, 3 g Manis pentadactyla L., 6 g Tea leaves and 15 g Zizyphus jujuba Mill. The obtained mixture was cooled and filtered to remove solid materials to obtain about 140 ml aqueous extract of the composition. 150 g grains consisting of 75 g Sorghum and 75 g Beams was used, and 50 g of which was soaked in the aqueous extract obtained above for 48 hours. Then, the mixture was filtered and dried.

The materials obtained in the above steps (1), (2) and (3) respectively were mixed thoroughly and then filled into a white, pure cotton bag to obtain the health-protective bag of the present invention.

Example 2

The procedure as same as that in Example 1 was repeated except that instead of using 150 g of the mixture of Sorghum and beans which had a weight proportion of 1:1, 100 g of the mixture of Sorghum, beans, panicum, miliaceum and millet which had a weight proportion of 1:1:1:1 was used, and 40 g of the mixture was soaked in said aqueous extract for 44 hours. The color of the bag was black.

Example 3

The procedure as same as that in Example 1 was repeated except that in step (2), instead of using 500 g rice, 450 g rice which had been stored for three years was used, and 150 g of which was soaked in said aqueous extract; in step (3), instead of using 150 g of the mixture of Sorghum and beans which had a weight proportion of 1:1, 100 g of the mixture of Sorghum, beans, and millet which had a weight proportion of 1:1:1 was used, and 40 g of the mixture was soaked in said aqueous extract for 60 hours. The color of the bag was green.

Example 4

The procedure as same as that in Example 1 was repeated except that in step (2), instead of using 500 g rice, 500 g rice which had been stored for three years was used, and 250 g of which was soaked in said aqueous extract; in step (3), instead of using 150 g of the mixture of Sorghum and beans which had a weight proportion of 1:1, 120 g of the mixture of Sorghum, beans, panicum miliaceum and millet which had a weight proportion of 1:1:1:1 was used, and 40 g of the mixture was soaked in said aqueous extract for 60 hours. The color of the bag was yellow.

Example 5

The procedure as same as that in Example 1 was repeated except that the color of the bag was red.

Example 6

The procedure as same as that in Example 1 was repeated except that 25 g ginseng and 30 g Astragalus membranaceus (Fisch.) Bunge were further added into the powder composition of step (1).

Example 7

The procedure as same as that in Example 1 was repeated except that the amounts of various components of the composition in step (1) were changed to:

8 g *Panax pseudo ginseng* Wall. Var. notoginseng (Burk.) Hoo et Tseng, 22 g *Rheum palmatum* L., 12 g *Aquilaria agallochah* Roxdb., 12 g *Angelica senensis* (Oliv) Diels, 12 g Saussurea Lappa Clarke, 12 g *Manis pentadactyla* L., 12 g *Carthamus tinctorius* L., 10 g *Prunus persica,* 10 g *Procirus trifoliata* (L.) Raf., 10 g *Notopterygium incisium* Ting, 15 g *Eucommia ulmoides,* 10 g Cinnamomum Cassia presl., 10 g *Achyrantes bidentata* Bl., 5 g *Kochia scoparia* (L.) Schrad., 10 g *Saposhnikovia divaricata* (Turcz.) Schisch K., 15 g *Melia toosendan* Sieb. et Zucc, 10 g *Schizandra chinensis* Baill., 25 g *Lycopodium clavatum* L., 8 g *Vaccaria pyramidata* Medic, 10 g *Lespedeza cuneata* (Dum. Cours.), 2 g *Blumea balsamifera* DC., 12 g *Periploca sepium* Bge., 10 g *Phyllostachis nigra* var. henonis (Miff.) Stapf. ex Rendle.

ucts in the prior art, it can be used on any parts of the human body.

(3) The use of the health-protective bag of the present invention is not restricted neither by time, location, working environment nor living environment. It can be used everywhere at any time. By using the health-protective bag of the present invention, one can strengthen the inner organ's function and the body's immunity by harmozined cooperation of acupuncture points, meridians and inner organs. Therefore, the health-protective bag of the present invention is not only good for health prevention but also effective for curing many different illnesses.

In the rehabilitation center of the "International Qi Gong University Emei Sichuan China" there have been 400 patients suffering from different diseases who fully relied on the use of the health-protective bag of the present invention to regain health. The results are presented in the following table:

| No. | type of illness | Number of cases | Nos. with notable eff. | Nos. with imp. eff. | Nos. with full eff. | No effects | Bag as used (Ex.) |
|---|---|---|---|---|---|---|---|
| 1 | Gastro enteritis | 30 | 4 | 5 | 21 | 0 | 1 |
| 2 | Hypertension | 17 | 3 | 4 | 10 | 0 | 3 |
| 3 | Hypotension | 29 | 6 | 8 | 15 | 0 | 5 |
| 4 | Anemia | 18 | 5 | 7 | 6 | 0 | 5 |
| 5 | Thrombocytopenia | 11 | 3 | 2 | 6 | 0 | 5 |
| 6 | Arthritis | 32 | 8 | 11 | 13 | 0 | 1 |
| 7 | Cardiac disease | 18 | 3 | 7 | 8 | 0 | 5 |
| 8 | Bronchitis | 21 | 2 | 13 | 6 | 0 | 7 |
| 9 | Emphysema | 10 | 2 | 2 | 6 | 0 | 7 |
| 10 | Pulmongery TBC | 13 | 4 | 3 | 6 | 0 | 1 |
| 11 | Skin disease | 8 | 2 | 2 | 4 | 0 | 1 |
| 12 | Myopia | 19 | 4 | 6 | 9 | 0 | 3 |
| 13 | Amblyopia | 8 | 3 | 2 | 3 | 0 | 3 |
| 14 | Glaucoma | 15 | 1 | 9 | 5 | 0 | 3 |
| 15 | Cystic hyperplasia of breast | 20 | 4 | 5 | 11 | 0 | 1 |
| 16 | Colelithiasis | 6 | 2 | 1 | 3 | 0 | 3 |
| 17 | Hepatitis | 16 | 3 | 5 | 8 | 0 | 3 |
| 18 | Osteitus ossificans | 4 | 1 | 1 | 2 | 0 | 3 |
| 19 | Tumor | 8 | 2 | 2 | 4 | 0 | 1 |
| 20 | Ischias | 11 | 2 | 4 | 5 | 0 | 1 |
| 21 | Diabetes | 6 | 2 | 1 | 3 | 0 | 4 |
| 22 | Neurasthenia | 21 | 3 | 5 | 13 | 0 | 6 |
| 23 | Neurotic headache | 12 | 1 | 3 | 8 | 0 | 6 |
| 24 | Nephritis | 6 | 2 | 1 | 3 | 0 | 4 |
| 25 | Apoplexy | 5 | 1 | 1 | 3 | 0 | 1 |
| 26 | Gastric ulcer | 7 | 2 | 3 | 2 | 0 | 6 |
| 27 | Meniere担 syndrome | 10 | 2 | 2 | 6 | 0 | 6 |
| 28 | Chloecystitis | 19 | 3 | 6 | 10 | 0 | 3 |
| | Total | 400 | 80 | 121 | 199 | 0 | |

THE ADVANTAGES OF THE INVENTION

As compared with the health-protective products in the prior art, the health-protective bag of the present invention has the following advantages:

(1) The health-protective bag of the present invention has no side-effects. It is reliable and safe. All components and ingredients are natural material, so they do not cause any adverse irritation to the human body.

(2) The health-protective bag of the present invention has overcome the restrictions of the health-protective prod- Throughout the foregoing specification many of the plant ingredients have been identified for completeness of disclosure by their full names including abbreviated terms and parenthetical designations indicating the persons who nominated such plants. Such abbreviations and parenthetical terms may be deleted without changing the meaning of the specification and without altering the Latin designations given to such plant. Using only their Latin names, the ingredients identified in this specification are as follows: (1) *Mellia toosendan,* (2) *Chrysanthemum indicum,* (3) *Lespedeza cuneata,* (4) *Phyllostachys nigra* var. henonis, (5)

Milletia reticulata, (6) Lygodium japonicum, (7) Pholidota chinensis, (8) Rheum palmatum, (9) Cibotium barometz, (10) Zingiber officinale, (11) Bai Cao Shuang, (12) Polygonum multiflorum, (13) Realgar, (14) Manis pentadactyla, (15) Ziziphus jujuba, (16) Panax Pseudo ginseng var. notoginseng, (17) Aquilaria agallochah, (18) Angelica sinensis, (19) Saussurea Lappa, (20) Carthamus Tinctoprius, (21) Prunus persica, (22) Procirus trifoliata, (23) Notopterygium incisium, (24) Eucommia ulmoides, (25) Cinnamomum Cassia, (26) Achyrantes bidentata, (27) Kochia scoparia, (28) Saposhnikovia divaricata, (29) Schizandra chinensis, (30) Lycopodium clavatum, (31) Vaccaria segetalis, (32) Blumea balsamifera and (33) Periploca sepium.

Additional advantages and modifications will readily occur to those skilled in the art. Therefore, the invention is not limited to the specific details, illustrated examples shown and described herein. Accordingly, various modifications may be made without departing from the spirit or scope of the general inventive concept as defined by the appended claims.

What is claimed is:

1. A health-protective bag which comprises a cotton bag and a composition contained in the bag, characterized in that said composition comprises the following ingredients:
   (a) 30–50% by weight of rice, wherein at least 30% of the rice has been soaked with an aqueous extract of the following Chinese herb composition for about 1–3 hours:
      13.00–14.00% Mekkis toosendan, 13.00–14.00% Chrysanthemum indicum, 7.60–8.60% Lespedeza cuneata, 3.50–4.50% Phyllostachys nigra var. henonis, 13.00–14.00% Milletia reticulata, 13.00–14.00% Lygodium japonicum, 7.60–8.60% Pholidota chinensis, 13.00–14.00%. Rheum palmatum, 7.60–8.60% Cibotium barometz, 3.50–4.50% Zingiber officinale, wherein all the percentages are weight percentages, and then dried after filtration;
   (b) 20–30% by weight of at least one grain selecting from the group consisting of Sorghum, Beams, panicum miliaceum and millet, wherein, at least 30% by weight of the grain has been soaked with an aqueous extract of the following Chinese herb composition for about 24–72 hours:
      40.60–41.60% Bai Cao Shuang, 8.00–8.40% Bamboo blossoms, 13.20–14.20% Polygonum multiflorum, 4.00–4.20% Realgar, 4.00–4.20% Manis pentadactyla, 8.00–8.40% Tealeaves and 20.00–21.00% Ziziphus jujuba, wherein all the percentages are weight percentages, and then dried after filtration;
   (c) 20–50% by weight of Chinese herb composition powder containing the following components:
      1.5–2.5% Panax pseudo ginseng var. notoginseng, 6.5–7.5% Rheum palmatum, 3.0–4.0% Aquilaria agallochah, 3.0–4.0% Angelica sinensis, 3.0–4.0% Saussurea Lappa, 4.8–5.5% Manis pentadactyla, 2.7–3.5% Carthamus Tinctoprius, 2.7–3.5% Prunus persica, 4.8–5.5% Procirus trifoliata, 4.8–5.5% Notopterygium incisium, 4.8–5.5% Eucommia ulmoides, 4.8–5.5% Cinnamomum Cassia, 3.0–4.0% Achyrantes bidentata, 1.5–2.5% Kochia scoparia, 3.0–4/-% Saposhnikovia divaricata, 4.8–5.5% Melia toosendan, 3.0–4.0% Schizandra chinensis, 10.1–11.1% Lycopodium clavatum, 2.7–3.5% Vaccaria segetalis, 4.8–5.5% Lespedeza cuneata, 1.0–1.5% Blumea balsamifera, 4.8–5.5% Periploca sepium, 3.0–4.0% Phyllostachis nigra var. henonis, wherein all the percentages are on the basis of the total weight of said composition.

2. The health-protective bag according to claim 1, characterized in that the said rice is the one which has been stored for at least three years.

3. The health-protective bag according to claim 1, characterized in that the bag contains 35–45% by weight of rice, 15–25% by weight of at least one grain selected from the group consisting of Sorghum, Beans, panicum miliaceum and millet and 30–40% by weight of Chinese herb composition powder.

4. The health-protective bag according to claim 1, characterized in that the color of the bag is white, black, yellow, green or red.

5. The health-protective bag according to claim 1, characterized in that the pulverous Chinese herb composition contained in the bag comprises:
   1.8–2.2% Panax pseudo ginseng var. notoginseng, 6.8–7.2% Rheum palmatum, 3.3–3.7% Aquilaria agallochah, 3.3–3.7% Angelica sinensis, 3.3–3.7% Saussurea Lappa, 5.1–5.3% Manis pentadactyla, 3.0–3.2% Carthamus tinctoprius, 3.0–3.2% Prunus persica, 5.1–5.2% Procirus trifoliata, 5.1–5.2% Notopterygium incisium, 5.1–5.3% Eucommia ulmoides, 5.1–5.3% Cinnamomum Cassia, 3.3–3.7% Achyrantes bidentata, 1.8–2.2% Kochia scoparia, 3.3–3.7% Saposhnikovia divaricata, 5.1–5.3% Melia toosendan, 3.3–3.7% Schizandra chinensis, 10.4–10.8% Lycopodium clavatum, 3.0–3.3% Vaccaria, segetalis 5.1–5.3% Lespedeza cuneata, 1.2–1.4% Blumea balsamifera, 5.1–5.3% Periploca sepium, 3.3–3.7% Phyllostachis nigra var. henonis, wherein all the percentages are weight percentages.

6. A process for producing the health-protective bag of the present invention, which comprises the following steps:
   (A) selecting a rice free from mildew and mould, wherein at least 30% by weight of which is treated according to the following method:
      (a) cooking the following Chinese herb composition in water for 1 to 3 hours:
         1300–1400% Melia toosendan, 13.00–14.00% Chrysanthemum indicum, 7.60–8.60% Lespedeza cuneata, 3.50–4.50% Phyllostachys nigra var. henonis, 13.00–14.00% Milletia reticulata, 13.00–14.00% Lygodium japonicum, 7.60–8.60% Pholidota chinensis, 13.00–14.00% Rheum palmatum, 7.60–8.60% Cibotium barometz, 3.50–4.50% Zingiber officinale Rose, wherein all the percentages are weight percentages; filtering the mixture after cooling to remove solid materials to obtain an aqueous extract of said composition;
      (b) soaking the rice with the aqueous extract obtained in the above step (a) at a weight ratio of aqueous extract: rice=30.50:70–50 for about 1–3 hours, drying the soaked rice after filtration;
   (B) selecting at least one grain from the group consisting of whether sorghum, beans, panicum, miliaceum and millet, wherein at least 30% by weight of which is treated according to the following method:
      (a) cooking the following Chinese herb composition in water for about 1 to 3 hours:
         40.60–41.60% Bai Cao Shuang, 8.00–8.40% Bamboo blossoms, 1.320–14.20% Polygonum multiflorum, 4.00–4.20% SnS, 4.00–4.20% Manis pentadactyla, 8.00–8.40% Tea Leaves and 20.00–21.00% *Ziziphus jujuba,* wherein all the percentages are weight percentages; filtering the mixture after cooling to remove solid materials to obtain an aqueous extract of said composition;

(b) soaking the selected grains(s) with the aqueous extract obtained in the above step (a) at a weight ratio of aqueous extract: grain(s)=40–60:60–40 for about 24–72 hours, drying the soaked grain(s) after filtration;

(C) pulverizing the following components respectively: *Panax pseudo ginseng* var. notoginseng, *Rheum palmatum, Aquilaria agallochah, Angelica sinensis,* Saussurea Lappa, *Manis pentadactyla, Carthamus tinctoprius, Prunus persica, Pocirus trifoliata, Notopterygium incisium, Eucommia ulmoides,* Cinnamomum Cassia, *Kochia scoparia, Saposhnikovia divaricata, Milia toosendan, Schizandra chinensis, Lycopodium clavatum, Vaccaria pyramidata* Medic, *Lespedeza cuneata, Blumea balsamifera, Periploca sepium, Phyllostachis nigra* var. henonis to make powders having particle size in the range of about 0.06 mm–0.10 mm, mixing these powders according to the following proportion to obtain a powder mixture:

1.5–2.5% *Panax pseudo ginseng* var. notoginseng, 6.5–7.5% *Rheum palmatum,* 3.0–4.0% *Aquilaria agallochah,* 3.0–4.0% *Angelica sinensis,* 3.0–4.0% Saussurea Lappa, 4.8–5.5% *Manis pentadactyla,* 2.7–3.5% *Carthamus tinctoprius,* 2.7–3.5% Prunus Persica, 4.8–5.5% *Procirus trifoliata,* 4.8–5.5% *Notopterygium incisium,* 4.8–5.5% *Eucommia ulmoides,* 4.8–5.5% Cinnamomum Cassia, 3.0–4.0% *Achyrantes bidentata,* 1.5–2.5% *Kochia scoparia,* 3.0–4.0% *Saposhnikovia divaricata,* 4.8–5.5% *Melia toosendan,* 3.0–4.0% *Schizandra chinensis,* 10.1–11.1% *Lycopodium clavatum,* 2.7–3.5% *Vaccaria pyrmidata,* 4.8–5.5% *Lespedeza cuneata,* 1.0–1.5% *Blumea balsamifera,* 4.8–5.5% *Periploca sepium* 3.0–4.0% *Phyllostachis nigra* var. henonis, wherein all the percentages are weight percentages;

(D) mixing thoroughly the rice, the grain(s) and the Chinese herbs composition powder obtained in the above steps (A), (B) and (C), respectively according to weight ratios of 30–50, 20–30, and 20–50;

(E) filling the composition obtained in step (D) into a pure cotton bag.

7. The process according to claim 6, characterized in that the said rice is the one which has been stored for at least three years.

8. The process according to claim 6, characterized in that the bag is prepared to contain 35–45% by weight of rice, 15–25% by weight of at least one grain selecting from the group consisting of Sorghum, Beans, panicum miliaceum and millet and 30–40% by weight of powder Chinese herb composition.

9. The process according to claim 6, characterized in that the color of the bag is prepared to be of white, black, yellow, green or red.

10. The process according to claim 6, characterized in that the bag is prepared to contain a Chinese herb composition powder having the following composition:

1.8–2.2% *Panax pseudo ginseng* var. notoginseng, 6.8–7.2% *Rheum palmatum,* 3.3–3.7% *Aquilaria agallochah,* 3.3–3.7% *Angelica sinensis,* 3.3–3.7% Saussurea Lappa, 5.1–5.3% *Manis pentadactyla,* 3.0–3/2% *Carthamus tinctorius,* 3.0–3.2% *Prunus persica,* 5.1–5.2% *Procirus trifoliata,* 5.1–5.2% *Notopterygium incisium,* 5.1–5.3% *Eucommia ulmoides,* 5.1–5.3% *Cinnamomum Cassia,* 3.3–3.7% *Achyrantes bidentata,* 1.8–2.2% *Kochia coparia,* 3.3–3.7% *Saposhnikovia divaricata,* 5.5–5.3% *Melia toosendan,* 3.3–3.7% *Schizandra chinensis,* 10–4–10.8% *Lycopodium clavatum,* 3.0–3.3% *Vaccaria pyrmidata,* 5.1–5.3% *Lespedeza cuneata,* 1.2–1.4% *Blumea balsamifera,* 5.1–5.3% *Periploca sepoum,* 3.3–3.7% *Phyllostachis nigra* var. henonis, wherein all the percentages are weight percentages.

* * * * *

UNITED STATES PATENT AND TRADEMARK OFFICE
CERTIFICATE OF CORRECTION

PATENT NO. : 6,123,946
DATED : September 26, 2000
INVENTOR(S) : Wei

It is certified that error appears in the above-indentified patent and that said Letters Patent is hereby corrected as shown below:

In column 3, line 33, "cooing" should read --cooling--.

In column 5, line 33, delete --whether--.

In column 6, line 39, "shit" should read --suit--;
line 58, "form" should read --from--.

In column 8, line 49, "preservers" should read --perseveres--.

In column 9, line 6, "erect" should read --effect--.

In column 10, line 4 "form" should read --from--.

In column 12, line 10, "harmozined" should read --harmonized--.

In claim 1, line 19, "Beams" should read --Beans--.

Signed and Sealed this

First Day of May, 2001

Attest:

NICHOLAS P. GODICI

Attesting Officer     Acting Director of the United States Patent and Trademark Office